(12) United States Patent
Huh

(10) Patent No.: US 8,208,959 B2
(45) Date of Patent: Jun. 26, 2012

(54) ANTI-BLINDING DEVICE HAVING WIRELESS COMMUNICATION FUNCTION

(75) Inventor: Moon Young Huh, Seoul (KR)

(73) Assignee: Otos Wing Co., Ltd. (KR)

( * ) Notice: Subject to any disclaimer, the term of this patent is extended or adjusted under 35 U.S.C. 154(b) by 0 days.

(21) Appl. No.: 12/950,531

(22) Filed: Nov. 19, 2010

(65) Prior Publication Data

US 2011/0159918 A1    Jun. 30, 2011

(30) Foreign Application Priority Data

Dec. 24, 2009  (KR) .................. 10-2009-0130323

(51) Int. Cl.
*H04M 1/00* (2006.01)
(52) U.S. Cl. ........................... 455/556.1; 2/8.2
(58) Field of Classification Search .................. None
See application file for complete search history.

(56) References Cited

U.S. PATENT DOCUMENTS

| | | | | |
|---|---|---|---|---|
| 6,070,264 A * | 6/2000 | Hamilton et al. | ................ | 2/8.8 |
| 8,068,881 B2 * | 11/2011 | Schrager | ................ | 455/569.1 |
| 2003/0130016 A1 * | 7/2003 | Matsuura et al. | ............ | 455/569 |
| 2004/0096078 A1 * | 5/2004 | Lin | ................ | 381/333 |
| 2010/0045928 A1 * | 2/2010 | Levy | ............... | 351/158 |
| 2010/0105364 A1 * | 4/2010 | Yang | ................ | 455/414.1 |
| 2011/0130176 A1 * | 6/2011 | Magrath et al. | ............... | 455/570 |

\* cited by examiner

*Primary Examiner* — Rafael Pérez-Gutiérrez
*Assistant Examiner* — German Viana Di Prisco
(74) *Attorney, Agent, or Firm* — Cantor Colburn LLP

(57) ABSTRACT

Disclosed is an anti-blinding device having a wireless communication function to allow a user to conveniently use a wireless communication cellular phone during operation. The anti-blinding device includes a main control device, a light transmission control device, first and second receiving/transmitting unit to perform signal conversion and transmission between a cellular phone and the main control device, and voice input and output devices. The main control device outputs alarm light and a ringtone using a lamp and the voice output device if it is determined that a digital signal transmitted from the second receiving/transmitting unit is an incoming call signal, and if the digital signal is a voice signal, transmits the digital voice signal to the voice output device. Also, the main control device transmits the digital voice signal from the voice input device to the second receiving/transmitting unit to enable a voice call.

2 Claims, 4 Drawing Sheets

ANTI-BLINDING DEVICE HAVING WIRELESS COMMUNICATION FUNCTION

BACKGROUND OF THE INVENTION

1. Field of the Invention

The present invention relates to an anti-blinding device, and more particularly, to an anti-blinding device having a wireless communication function to allow a user to conveniently use a wireless communication cellular phone even during implementation of an operation.

2. Description of the Related Art

Generally, during a welding, cutting, or grinding operation, a welding helmet is used to protect the welder's eyes from glare and various toxic substances. Recently, a variety of kinds of safe and convenient electronic welding helmets have been developed and used.

FIG. 1 is a perspective view illustrating a conventional welding helmet including an anti-blinding device. As illustrated in FIG. 1, the conventional welding helmet 1 includes a welding-light detection anti-blinding device 2 worn on the welder's head to control exposure to light emitted from a welding or cutting torch.

The conventional welding helmet 1, which is provided at a front surface thereof with the anti-blinding device 2, may reduce the illumination intensity of light directed to the welder's eyes using an anti-blinding plate 5 that is a Liquid Crystal Display (LCD) included in the anti-blinding device 2.

Specifically, the anti-blinding device 2 further includes a photo sensor 4, such as, e.g., a photodiode attached to a front surface thereof. The photo sensor 4 is adapted to sense light emitted from a welding or cutting torch. As a control circuit mounted in the anti-blinding device 2 controls the liquid crystal display, i.e. the anti-blinding plate 5 to be darkened such that the illumination intensity of light passing through the anti-blinding plate 5 is reduced, the anti-blinding device 2 may serve to protect the eyes of a welder who wears the welding helmet 1.

The above described conventional electronic welding helmet including the anti-blinding device has been developed to provide the welder with a fixed darkness degree of a shutter (i.e. the anti-blinding plate), or to change a darkness degree of the shutter to a standard level according to a welding operation environment. The conventional electronic welding helmet also enables not only control of a shutter operation to shield welding light, but also variable control of a shutter delay time to prevent the welder's eyes from being blinded by light emitted from a base metal after welding. In addition, a variety of control switches or variable adjustment switches required for the shutter operation are provided at specific positions of the electronic welding helmet to maximize convenience of use by the welder.

However, when using the above described conventional welding helmet having the anti-blinding device, even if a cellular phone rings while a welder is performing a welding operation, the welder may have difficulty hearing a ringtone due to high levels of ambient noise. This, in particular, may cause a serious problem in relation to an emergency call. In addition, the welder must inconveniently stop what they are doing and remove the welding helmet in order to receive the call.

SUMMARY OF THE INVENTION

Therefore, the present invention has been made in view of the above problem, and it is an object of the present invention to provide an anti-blinding device having a wireless communication function to allow a user to conveniently use a wireless communication cellular phone even during implementation of an operation.

In accordance with an aspect of the present invention, the above and other objects can be accomplished by the provision of an anti-blinding device having a wireless communication function, including a light detecting device to measure the luminance of light based on a signal input from a photo sensor, in order to protect the welder's eyes from light generated from a welding or cutting torch, a control switch to input a user command, a main control device to set a reference value required to control the detection sensitivity of the light detecting device in response to the user command input from the control switch and also, to set a light transmittance and operation delay time of an anti-blinding plate, the main control device determining generation of welding light if the luminance of light detected by the light detecting device is a preset reference value or more and thus operating a light transmission control device, a light transmission control device to operate the anti-blinding plate according to the light transmittance set by the main control device so as to allow the anti-blinding plate to maintain a constant light transmittance value, a first receiving/transmitting unit to receive and convert an incoming call signal of a cellular phone and a user voice signal into a wireless signal and transmit the wireless signal to a second receiving/transmitting unit and also, to convert a wireless signal transmitted from the second receiving/transmitting unit into a digital signal and transmit the digital signal to the cellular phone to enable implementation of a voice call, the second receiving/transmitting unit to convert a wireless signal transmitted from the first receiving/transmitting unit into a digital signal and transmit the digital signal to the main control device and also, to convert a digital signal transmitted from the main control device into a wireless signal and transmit the wireless signal to the first receiving/transmitting unit, a voice output device to convert a digital voice signal transmitted from the main control device so as to output voice that is previously input by a user, and a voice input device to input and transmit a user voice command to the main control device, wherein the main control device analyzes the digital signal transmitted from the second receiving/transmitting unit, and if it is determined that the digital signal is the incoming call signal, turns on a lamp provided inside the anti-blinding device and simultaneously, outputs a ringtone through the voice output device and also, transmits the digital voice signal, transmitted from the second receiving/transmitting unit, to the voice output device, and wherein the main control device transmits the digital voice signal, converted from the user voice signal input through the voice input device, to the second receiving/transmitting unit to enable implementation of a voice call.

The voice output device may include a voice information database to store the digital voice signal transmitted from the main control device and output a voice signal, an amplifier to amplify the digital voice signal transmitted from the main control device or the voice signal output from the voice information database, and a speaker to output voice amplified by the amplifier to the outside so as to allow the user to hear the voice.

The voice input device may include a microphone to receive user voice, a filter to filter the voice input through the microphone, and a digital voice input signal processor to convert an analogue voice signal, input through the filter, into a digital signal.

The first receiving/transmitting unit and the second receiving/transmitting unit may adopt a Bluetooth communication method.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Hereinafter, an exemplary embodiment of the present invention will be described in detail with reference to the accompanying drawings.

The terms or words used in the specification and claims of the present invention are not interpreted using typical or dictionary limited meanings, and are constructed as meanings and concepts conforming to the technical sprit of the present invention based on the principle that the inventors can appropriately define the concepts of the terms to explain the present invention in the best manner. Accordingly, it is to be understood that the detailed description, which will be disclosed along with the accompanying drawings, is intended to describe the exemplary embodiments of the present invention and is not intended to represent all technical ideas of the present invention. Therefore, it should be understood that various equivalents and modifications can exist which can replace the embodiments described in the time of the application. Also, the same reference numbers used throughout the drawings refer to the same or like parts.

Figure 1:
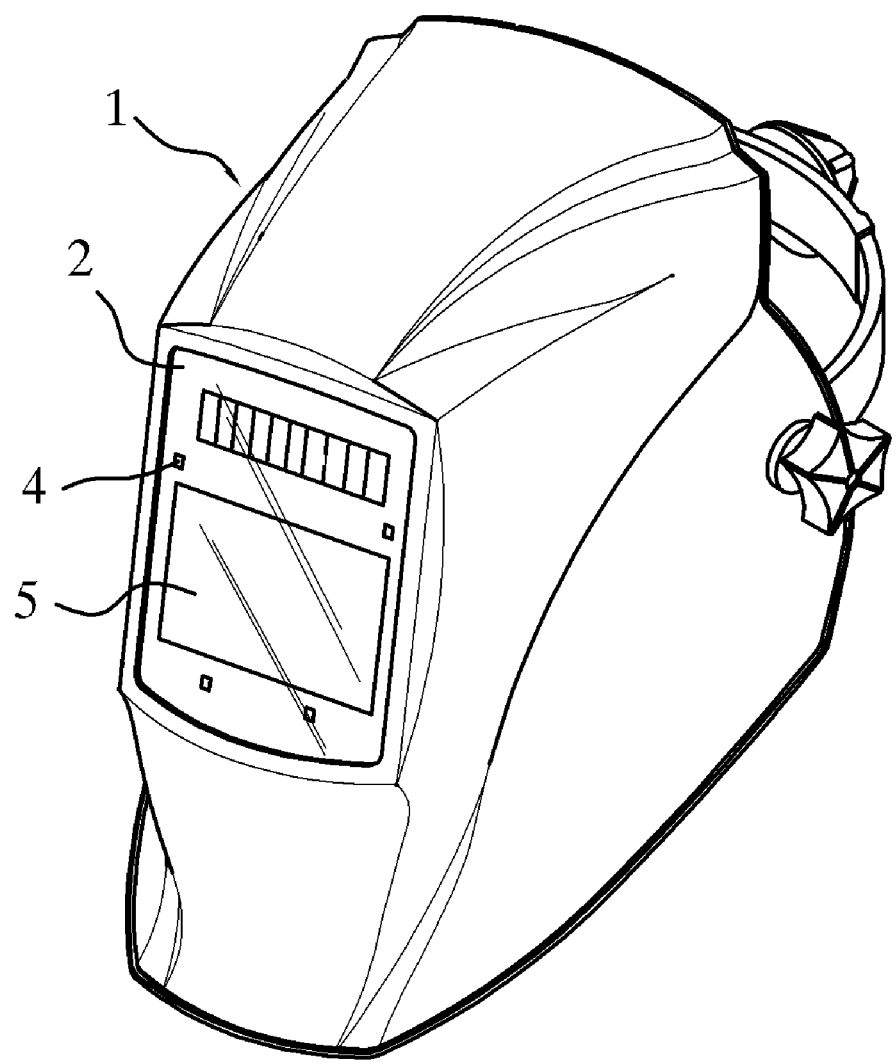
FIG. 1 is a perspective view illustrating a conventional welding helmet having an anti-blinding device.
Figure 2:
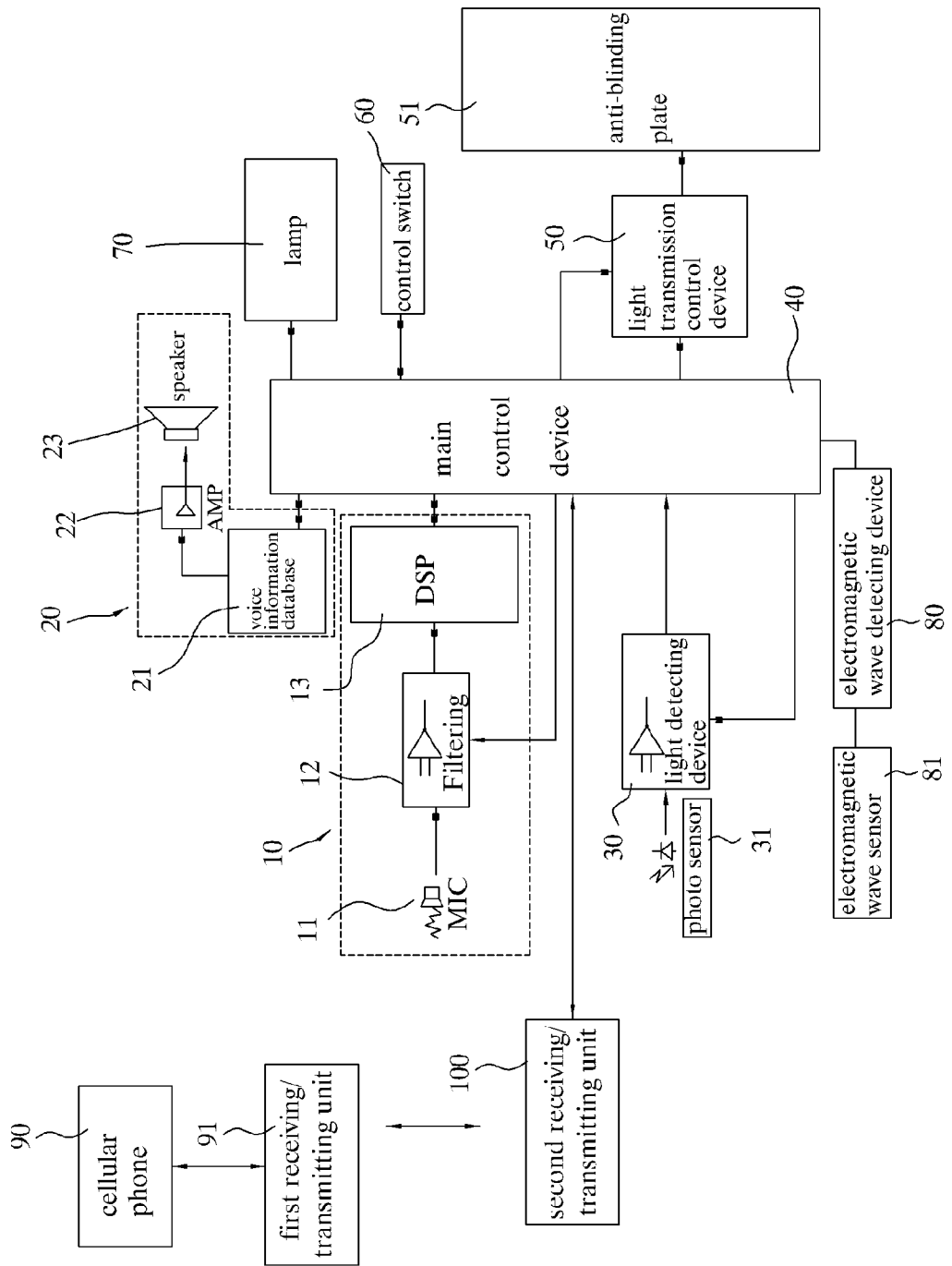
FIG. 2 is a block diagram illustrating an anti-blinding device having a wireless communication function according to the present invention.
Figure 3:
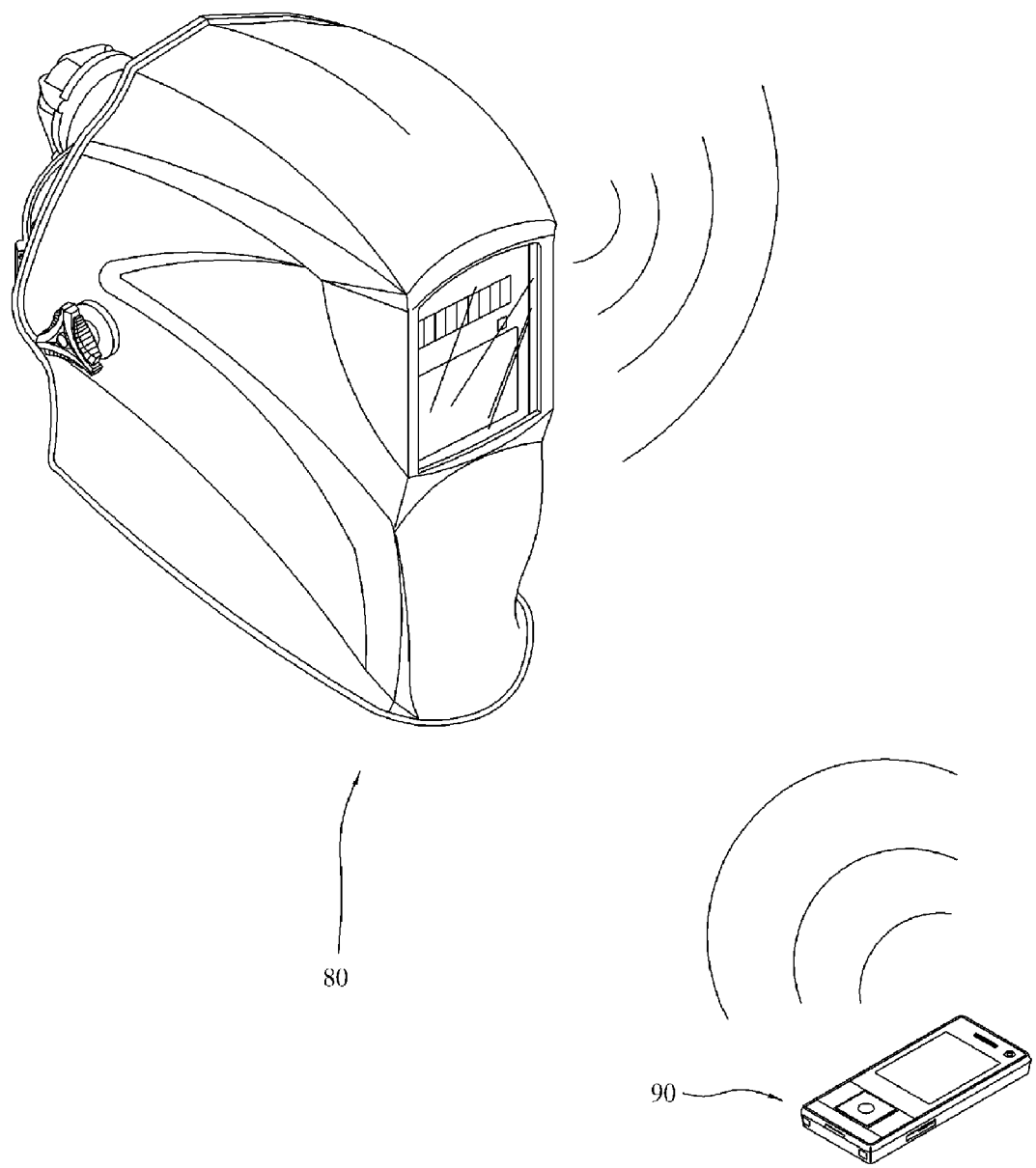
FIGS. 3 and 4 are views illustrating an embodiment of the present invention in use.
Figure 4:
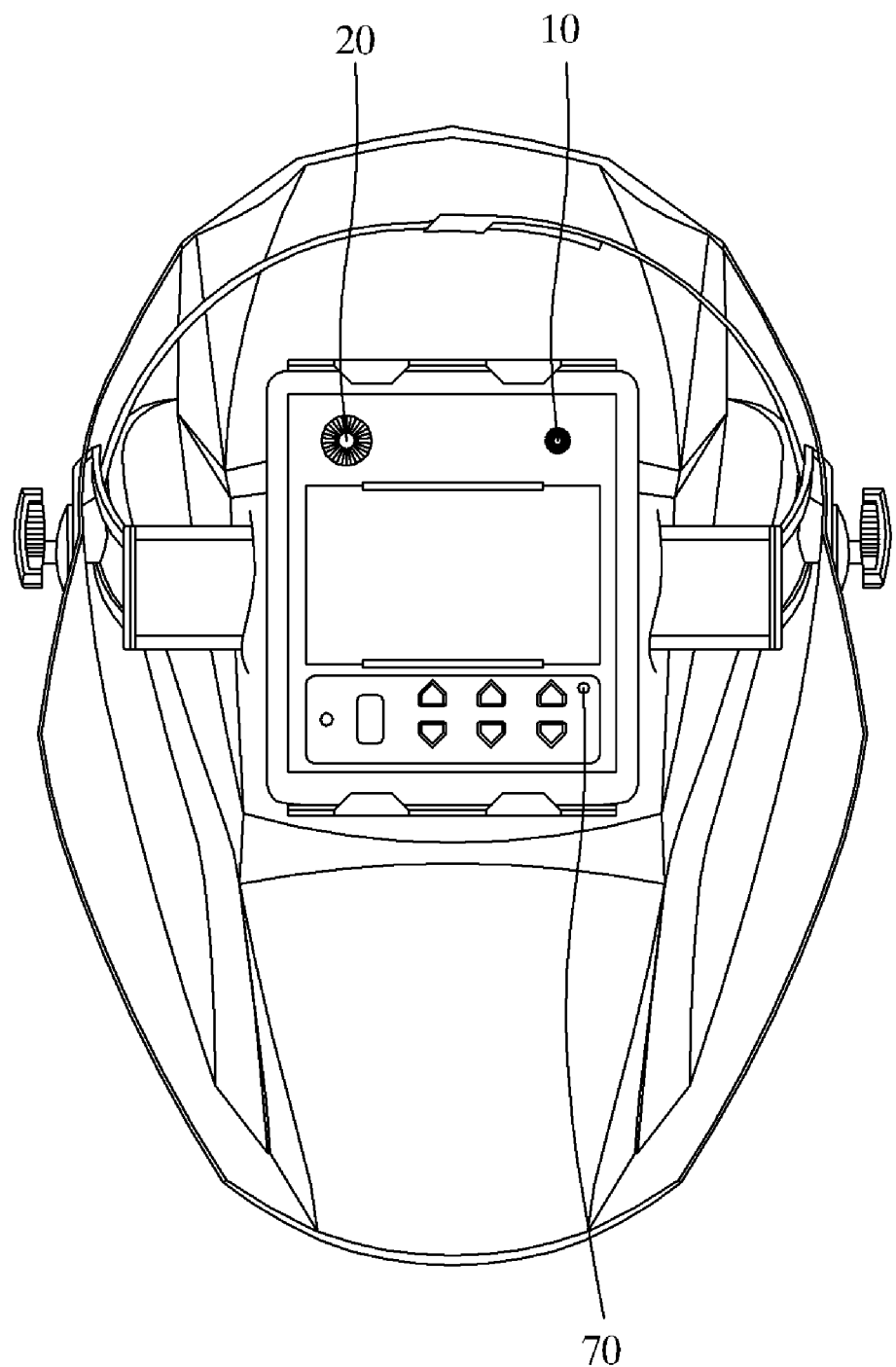

FIG. 2 is a block diagram illustrating an anti-blinding device having a wireless communication function according to the present invention, and FIGS. 3 and 4 are views illustrating an embodiment of the present invention in use.

As illustrated, the anti-blinding device of the present invention includes a voice input device 10 including a microphone 11, a filter 12, and a Digital input voice Signal Processor (DSP) 13, a voice output device 20 including a voice information database 21, an amplifier 22, and a speaker 23, a light detecting device 30, a photo sensor 31, a main control device 40, a light transmission control device 50, an anti-blinding plate 51, a control switch 60, a lamp 70, an electromagnetic wave detecting device 80, an electromagnetic wave sensor 81, a cellular phone 90, a first receiving/transmitting unit 91, and a second receiving/transmitting unit 100.

The light detecting device 30 serves to detect the luminance of light based on a signal input from the photo sensor 31. More particularly, the light detecting device 30 serves to detect light generated from a welding or cutting torch.

The main control device 40 functions to set a reference value required to control the detection sensitivity of the light detecting device 30 based on an input signal from the control switch 60 and also, to set a light transmittance and operation delay time of the anti-blinding plate 51. If the luminance of light detected by the light detecting device 30 is a preset reference value or more, the main control device 40 determines that the light is welding light, and then, operates the light transmission control device 50 based on the determined result. To this end, the main control device 40 is preferably a microcomputer.

The light transmission control device 50 operates the anti-blinding plate 51 based on the light transmittance set by the main control device 40, so as to allow the anti-blinding plate 51 to keep a constant light transmittance value.

The electromagnetic wave sensor 81 serves to sense electromagnetic waves generated from the welding or cutting torch. After a signal input from the electromagnetic wave sensor 81 is subjected to resonance, the electromagnetic wave detecting device 80 compares the resonated signal with a reference value that is variably set.

Accordingly, in addition to operating the light transmission control device 50 in response to a user input signal through the control switch 60, the main control device 40 further monitors variation in electromagnetic signals output from the electromagnetic wave detecting device 80 to control operation of the light transmission control device 50.

The first receiving/transmitting unit 91 receives an incoming call signal of the cellular phone 90 and a user voice signal. Then, the first receiving/transmitting unit 91 converts the received signal into a wireless signal and transmits the wireless signal to the second receiving/transmitting unit 100. The first receiving/transmitting unit 91 further converts a wireless signal transmitted from the second receiving/transmitting unit 100 into a digital signal and transmits the digital signal to the cellular phone 90 to enable implementation of a voice call.

The second receiving/transmitting unit 100 receives and converts a wireless signal transmitted from the first receiving/transmitting unit 100 into a digital signal, and then, transmits the digital signal to the main control device 40. The second receiving/transmitting unit 100 further converts a digital signal transmitted from the main control device 40 into a wireless signal, and then, transmits the wireless signal to the first receiving/transmitting unit 91.

The main control device 40 analyzes the digital signal transmitted from the second receiving/transmitting unit 100. If it is determined that the digital signal is the incoming call signal, the main control device 40 turns on the lamp 70 to emit alarm light and simultaneously, outputs a ringtone through the voice output device 20. Also, the main control device 40 transmits a digital voice signal transmitted from the second receiving/transmitting unit 100 to the voice output device 20.

The voice output device 20 serves to output voice using the digital voice signal transmitted from the main control device 40. Here, the voice may be previously input by a user. To output voice, the voice output device 20 includes the voice information database 21, the amplifier 22 and the speaker 23.

The voice information database 21 stores and outputs the digital voice signal transmitted from the main control device 40. The amplifier 22 amplifies the digital voice signal transmitted from the main control device 40 or output from the voice information database 21. The speaker 23 outputs voice amplified by the amplifier 22 to the outside so as to allow the user to hear the amplified voice.

The voice input device 10 serves to input a user voice command. To this end, the voice input device 10 includes the microphone 11, the filter 12, and the digital input voice signal processor 13.

The microphone 11 receives the user voice command, the filter 12 filters the voice input through the microphone 11, and the digital voice input signal processor 13 converts an analogue voice signal, input through the filter 12, into a digital signal. In this case, the microphone 11 is preferably installed close to the mouth of the user to assure easy voice input.

The main control device 40 transmits the digital voice signal, converted from the user voice signal input through the voice input device 10, to the second receiving/transmitting unit 100.

The second receiving/transmitting unit 100 converts the digital signal transmitted to the main control device 40 into a wireless signal and transmits the wireless signal to the first receiving/transmitting unit 91. The first receiving/transmitting unit 91 converts the received wireless signal from the second receiving/transmitting unit 100 into a digital signal and transmits the digital signal to the cellular phone 90 to enable implementation of a voice call.

Preferably, the first receiving/transmitting unit 91 and the second receiving/transmitting unit 100 adopt a Bluetooth communication method.

As is apparent from the above description, through use of an anti-blinding device having a wireless communication function according to the present invention, if a cellular phone rings while a welder is performing a welding operation, the anti-blinding device can directly output light and a ringtone using a lamp and a voice output device, thereby easily notifying a user of the incoming call despite high levels of ambient noise, assuring rapid response to an emergency call.

Further, the user can conveniently talk on the cellular phone using the microphone and the speaker provided in the anti-blinding device without taking off a welding helmet even during implementation of an operation.

Furthermore, if necessary, it is possible to store a transmitted voice message or conversation of the cellular phone.

The above description related to the preferred embodiment of the present invention and the accompanying drawings has been provided for illustrative purposes, and is not intended to limit the scope of the present invention defined by the claims. Thus, those skilled in the art will appreciate that various modifications, additions and substitutions are possible, without departing from the scope and spirit of the invention as disclosed in the accompanying claims. Accordingly, the technical protection range of the present invention should be determined by the appended claims.

What is claimed is:

1. An anti-blinding welding helmet having a wireless communication function, comprising:
    a light detecting device to measure the luminance of light based on a signal input from a photo sensor, in order to protect the welder's eyes from light generated from a welding or cutting torch;
    a control switch to input a user command;
    a main control device to set a reference value required to control the detection sensitivity of the light detecting device in response to the user command input from the control switch and also, to set a light transmittance and operation delay time of an anti-blinding plate, the main control device determining generation of welding light if the luminance of light detected by the light detecting device is a preset reference value or more and thus operating a light transmission control device;
    a light transmission control device to operate the anti-blinding plate according to the light transmittance set by the main control device so as to allow the anti-blinding plate to maintain a constant light transmittance value,
    a first receiving/transmitting unit to receive and convert an incoming call signal of a cellular phone and a user voice signal into a wireless signal and transmit the wireless signal to a second receiving/transmitting unit and also, to convert a wireless signal transmitted from the second receiving/transmitting unit into a digital signal and transmit the digital signal to the cellular phone to enable implementation of a voice call;
    the second receiving/transmitting unit to convert a wireless signal transmitted from the first receiving/transmitting unit into a digital signal and transmit the digital signal to the main control device and also, to convert a digital signal transmitted from the main control device into a wireless signal and transmit the wireless signal to the first receiving/transmitting unit;
    a voice output device to output a digital voice signal transmitted from the main control device so as to output a voice command that is previously input by a user; and
    a voice input device to input and transmit a user voice command to the main control device,
    wherein the main control device analyzes the digital signal transmitted from the second receiving/transmitting unit, and if it is determined that the digital signal is the incoming call signal, turns on a lamp provided inside the anti-blinding welding helmet and simultaneously, outputs a ringtone through the voice output device and also, transmits the digital voice signal, transmitted from the second receiving/transmitting unit, to the voice output device,
    wherein the main control device transmits the digital voice signal, converted from the user voice signal input through the voice input device, to the second receiving/transmitting unit to enable implementation of a voice call,
    wherein the voice output device includes: a voice information database to store the digital voice signal transmitted from the main control device and a voice command signal input by a user; an amplifier to amplify the digital voice signal or the ringtone transmitted from the main control device or the voice command signal output from the voice information database;
    and a speaker to output voice amplified by the amplifier to the outside so as to allow the user to hear the voice, and
    wherein the voice input device includes: a microphone to receive user voice, the microphone disposed in a position corresponding to the mouth of a user of the welding helmet; a filter to filter the voice input through the microphone; and a digital voice input signal processor to convert an analogue voice signal, input through the filter, into a digital signal.

2. The anti-blinding device according to claim 1, wherein the first receiving/transmitting unit and the second receiving/transmitting unit adopt a Bluetooth communication method.

* * * * *